(12) United States Patent
Lv et al.

(10) Patent No.: US 12,290,404 B2
(45) Date of Patent: May 6, 2025

(54) INTERFACE IN COLOR DOPPLER ULTRASOUND SPECTRUM MODE, OPERATION METHOD, DEVICE, AND STORAGE MEDIUM

(71) Applicants: THE THIRD MEDICAL CENTER CHINESE PLA GENERAL HOSPITAL, Beijing (CN); Healson Technology Co., Ltd., Sichuan (CN)

(72) Inventors: Faqin Lv, Beijing (CN); Xiaoliang Li, Beijing (CN); Youquan Xiong, Sichuan (CN)

(73) Assignees: THE THIRD MEDICAL CENTER CHINESE PLA GENERAL HOSPITAL, Beijing (CN); HEALSON TECHNOLOGY CO., LTD., Sichuan (CN)

( * ) Notice: Subject to any disclaimer, the term of this patent is extended or adjusted under 35 U.S.C. 154(b) by 162 days.

(21) Appl. No.: 18/325,393

(22) Filed: May 30, 2023

(65) Prior Publication Data
US 2023/0301629 A1 Sep. 28, 2023

(30) Foreign Application Priority Data
Mar. 28, 2022 (CN) .......................... 202210312679.2

(51) Int. Cl.
*A61B 8/00* (2006.01)
*A61B 8/06* (2006.01)

(52) U.S. Cl.
CPC ................ *A61B 8/463* (2013.01); *A61B 8/06* (2013.01); *A61B 8/469* (2013.01); *A61B 8/488* (2013.01)

(58) Field of Classification Search
CPC ........... A61B 8/463; A61B 8/06; A61B 8/469; A61B 8/488
See application file for complete search history.

(56) References Cited

U.S. PATENT DOCUMENTS 5,163,434 A * 11/1992 Kumazawa .............. A61B 8/06
600/455
2015/0164478 A1* 6/2015 Jung .................... G01S 7/52063
600/443

(Continued)

OTHER PUBLICATIONS

Meola et al.; "Basics for performing a high-quality color Doppler sonography of the vascular access"; The Journal of Vascular Access vol. 22, Issue 1_suppl, Nov. 2021, pp. 18-31 (Year: 2021).*

*Primary Examiner* — Dixomara Vargas
(74) *Attorney, Agent, or Firm* — NKL Law; Allen Xue

(57) ABSTRACT

An interface in a color Doppler ultrasound spectrum mode is generated on a display screen. In the interface, at a sampling preparation stage, a plurality of sampling instruction receiving regions are generated on a first position where a part of pixels of sampling tools are located and other positions. Instructions given in the regions are configured to control the sampling tools to change sampling ranges and sampling directions and pulse repetition frequencies. At a blood flow spectrum display stage, the sampling instruction receiving regions are closed; and a blood flow spectrum image control instruction region is generated to change a position of a blood flow spectrum baseline, and change an ultrasound signal gain and a spectrum speed. A computer program is stored to implement the operation method for the above color Doppler ultrasound spectrum mode interface.

10 Claims, 11 Drawing Sheets

(56) References Cited

U.S. PATENT DOCUMENTS

| | | | |
|---|---|---|---|
| 2016/0247279 A1* | 8/2016 | Lavi | A61B 6/466 |
| 2019/0206050 A1* | 7/2019 | Yates | A61B 1/0669 |
| 2019/0365354 A1* | 12/2019 | Du | A61B 8/5284 |
| 2020/0397409 A1* | 12/2020 | Inoue | A61B 8/0858 |
| 2022/0400946 A1* | 12/2022 | Mujat | A61B 5/14555 |
| 2023/0023083 A1* | 1/2023 | Shelton, IV | A61B 17/00 |
| 2023/0181160 A1* | 6/2023 | Chiang | A61B 8/461 |
| | | | 600/444 |
| 2023/0329646 A1* | 10/2023 | Zhou | A61B 7/003 |

* cited by examiner

INTERFACE IN COLOR DOPPLER ULTRASOUND SPECTRUM MODE, OPERATION METHOD, DEVICE, AND STORAGE MEDIUM

FIELD

The present disclosure relates to the technical field of computers, in particular to an interface in a color Doppler ultrasound spectrum mode, an operation method, a device, and a storage medium.

BACKGROUND

Ultrasound equipment is generally large machinery equipment for medical places and has the characteristics of operation complexity and large size.

However, with the expansion of application scenarios, it is necessary to use ultrasound equipment in some non-fixed places, such as disaster relief sites, rapid medical disposal sites and household medical equipment, and lightweight ultrasound equipment is required in these scenarios.

When the ultrasound equipment is used in such scenarios, there is a need to satisfy core functions of the ultrasonic equipment, including control, read, calculation, display and interaction with respect to the ultrasound equipment.

However, there is no lightweight equipment supporting such a technology at present.

SUMMARY

In order to solve the above-mentioned technical problems, the present disclosure provides an interface in a color Doppler ultrasound spectrum mode, an operation method, a device, and a storage medium.

The interface in the color Doppler ultrasound spectrum mode provided by the present disclosure is generated on a display screen coupled to a processor.

For the interface:

(1) A blood flow ultrasound image display region is provided at a sampling preparation stage, and a blood flow ultrasound image display region and a blood flow spectrum image region are provided side by side at a blood flow spectrum display stage; and a plurality of sampling tools used to represent sampling ranges and sampling directions on blood flow ultrasound images are displayed at any stage, and the sampling tools overlap with the blood flow ultrasound images.

(2) At the sampling preparation stage, a plurality of sampling instruction receiving regions are generated on a first position where a part of pixels of the sampling tools are located and other positions excluding the first position on the interface; and instructions given in the sampling instruction receiving regions are configured to control the sampling tools to change sampling ranges, sampling directions and pulse repetition frequencies.

(3) At the blood flow spectrum display stage, the sampling instruction receiving regions are closed; a blood flow spectrum image control instruction region is generated in each of the blood flow ultrasound image display region and the blood flow spectrum image region; and the instructions given in the blood flow spectrum image control instruction regions are configured to change a position of a blood flow spectrum baseline, an ultrasound signal gain and a spectrum speed.

The interface in the color Doppler ultrasound spectrum mode as mentioned above is further described as follows: the plurality of sampling tools include:

(1) a parallelogram sampling frame located in the middle of the blood flow ultrasound image display region, and configured to determine a color Doppler ultrasound image region;

(2) a pair of horizontally-disposed parallel lines located in the sampling frame, forming a sampling volume tool, and configured to mark an intravascular sampling volume;

(3) a first line segment located between the parallel lines, forming a blood flow direction tool, and configured to mark a blood flow direction; and (4) a second line segment longitudinally passing through the sampling frame, forming a blood flow spectrum sampling line, and configured to mark a specific sampling position on a cross section of a blood vessel.

The interface in the color Doppler ultrasound spectrum mode as mentioned above is further described as follows: the description that the plurality of sampling instruction receiving regions are generated on the first position where a part of pixels of the sampling tools are located and other positions excluding the first position on the interface is specifically as follows:

(1) a first instruction receiving region for deflecting the blood flow direction tool is disposed at a position where pixels on at least one end of the first line segment and regions near the pixels are located;

(2) a second instruction receiving region for changing a position of the blood flow spectrum sampling line on the cross section of the blood vessel is disposed on a lower part of the interface;

(3) a third instruction receiving region for moving the sampling volume tool in any direction is disposed in regions excluding the first instruction receiving region in the interface; and (4) a fourth instruction receiving region for changing a pulse repetition frequency value and a sampling volume is disposed at any one of a left part and a right part of the blood flow ultrasound image display region.

The interface in the color Doppler ultrasound spectrum mode as mentioned above is further described as follows: the description that the blood flow spectrum image control instruction region is generated in each of the blood flow ultrasound image display region and the blood flow spectrum image region is specifically as follows: an ultrasound signal gain adjustment instruction receiving region is generated in the blood flow ultrasound image display region, and a baseline position and spectrum speed adjustment instruction receiving region is generated in the blood flow spectrum image region.

The display screen is a touch screen.

An operation method for the interface in the color Doppler ultrasound spectrum mode provided by the present disclosure is implemented on a display screen coupled to a processor. The method includes:

generating a color Doppler ultrasound spectrum sampling preparation interface on the display screen, displaying blood flow ultrasound images and sampling tools to a user in the interface, and generating sampling instruction receiving regions;

receiving instructions input by the user in the sampling instruction receiving regions, and changing one of sampling ranges, sampling directions and pulse repetition frequencies according to the instructions;

switching from the color Doppler ultrasound spectrum sampling preparation interface to a blood flow spectrum display interface, and closing the sampling instruction receiving regions;

displaying blood flow ultrasound images and blood flow spectrum images side by side as well as sampling tools overlapping with the blood flow ultrasound images in the interface to the user;

generating a blood flow spectrum image control instruction region in each of a blood flow ultrasound image display region and a blood flow spectrum image region; and receiving an instruction input by the user in the blood flow spectrum image control instruction region, and changing a position of a blood flow spectrum baseline and changing one of an ultrasound signal gain and a spectrum speed according to the instruction.

The operation method for the interface in the color Doppler ultrasound spectrum mode as mentioned above is further described as follows. The input is a sliding input by the user on the interface, is specifically a movement input by a mouse pointer, and is a touch input by the user on a display screen with a touch function via a finger tip, wherein a slide input trajectory includes:

(1) a first direction of movement approximately parallel to a pixel column in the interface;

(2) a second direction of movement approximately parallel to a pixel row in the interface;

(3) a third direction of arc movement around the center of the interface; and (4) a fourth direction not belonging to the first direction, the second direction and the third direction.

The operation method for the interface in the color Doppler ultrasound spectrum mode as mentioned above is further described as follows: the step of receiving the instructions input into the sampling instruction receiving regions by the user, and changing one of the sampling ranges, sampling directions and pulse repetition frequencies according to the instructions specifically includes:

when an instruction input by the user in a first instruction receiving region is received, calling a blood flow direction tool, and rotating the blood flow direction tool;

when an instruction input by the user in a second instruction receiving region is received, calling a blood flow spectrum sampling line, and adjusting a position on a cross section of a blood vessel; and when an instruction input by the user in a third instruction receiving region is received, calling a sampling volume tool, and moving the sampling volume tool.

The operation method for the interface in the color Doppler ultrasound spectrum mode as mentioned above is further described as follows: the touch input via the finger tip including single-point touch and multi-point touch; and when an multi-point touch instruction in a fourth instruction receiving region by the user is received, calling a sampling volume tool to change a sampling volume, or change a pulse repetition frequency value.

The operation method for the interface in the color Doppler ultrasound spectrum mode as mentioned above is further described as follows: the step of receiving the instruction input into the blood flow spectrum image control instruction region by the user, and changing the position of the blood flow spectrum baseline and one of the ultrasound signal gain and the spectrum speed according to the instruction specifically includes:

when an instruction input by the user in an ultrasound signal gain adjustment instruction receiving region is received, calling an ultrasound signal gain function to adjust ultrasound signal gain intensity;

when an instruction input by the user in a spectrum speed adjustment instruction region in a first direction is received, calling a baseline tool to change the position of the blood flow spectrum baseline; and when an instruction input by the user in the spectrum speed adjustment instruction region in a second direction is received, adjusting a spectrum tool to adjust the spectrum speed.

A storage medium provided by the present disclosure stores a computer program. The computer program is executed by hardware to implement the above-mentioned operation method for the interface in the color Doppler ultrasound spectrum mode.

A color Doppler ultrasound device provided by the present disclosure includes a display screen, a processor, a communication interface and an ultrasound transducer probe, wherein the touch screen is provided with the interface in the color Doppler ultrasound spectrum mode, and the communication interface communicates with the ultrasound transducer probe under the control of the processor.

The present disclosure has the beneficial effects as follows:

The present disclosure provides the interface in the color Doppler ultrasound spectrum mode. By generating a color Doppler ultrasound blood flow spectrum interface on the display screen and generating an instruction control region on the interface, the sampling tools for ultrasound signals are controlled in a manner of touch or mouse sliding to generate a processing command for controlling an ultrasound probe to control the ultrasound probe, thereby returning a required ultrasound signal.

The present disclosure provides a more convenient operation color Doppler ultrasound spectrum mode interface and provides a more convenient input method for a color Doppler ultrasound spectrum mode operation instruction.

The present disclosure can be implemented by adopting a conventional personal computer or a display device with a touch screen, without a special color Doppler ultrasound spectrum mode display device.

The device in the present disclosure is portable and wide in application scenario.

BRIEF DESCRIPTION OF THE DRAWINGS

In order to describe the technical solutions mentioned in the embodiments of the present disclosure more clearly, the accompanying drawings required for describing the embodiments will be briefly introduced below. However, the accompanying drawings in the following description show only some embodiments of the present disclosure, and those of ordinary skill in the art may easily derive other accompanying drawings from these accompanying drawings without creative efforts.

Figure 1:
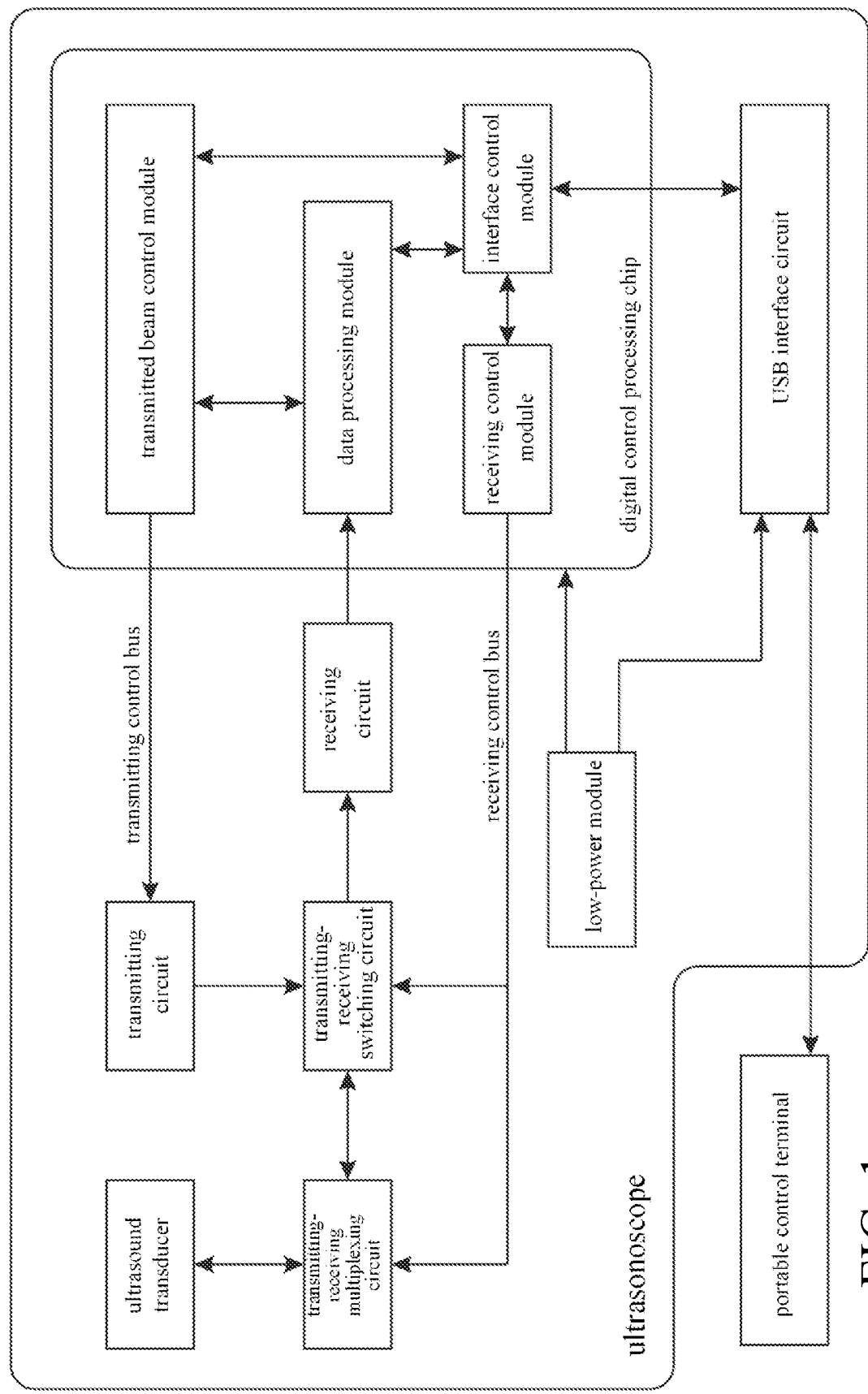
FIG. 1 is a structural diagram of ultrasound equipment in example 1.

In which:

display screen 1; interface 2 at sampling preparation stage; interface 3 at blood flow spectrum display stage; first button 10; interface 11 in color Doppler ultrasound spectrum mode; finger tip contact surface 13; other functional region 14; multi-point touch 15; blood flow direction tool 21; blood flow spectrum sampling line 22; sampling frame 23; sampling volume tool 24; blood vessel 25; blood flow ultrasound image display region 31; blood flow spectrum image region 32; blood flow spectrum image 33; baseline 34; first direction 41; second direction 42; third direction 43; fourth direction 44; first instruction receiving region 91; second instruction receiving region 92; third instruction receiving region 93; fourth instruction receiving region 94; fifth instruction receiving region 95; and sixth instruction receiving region 96.

DETAILED DESCRIPTION OF THE EMBODIMENTS

In order to make objectives, technical solutions and advantages of the embodiments of the present disclosure clearer, the technical solutions in the embodiments of the present disclosure will be described clearly and completely below in conjunction with the accompanying drawings in the embodiments of the present disclosure. Obviously, the described embodiments are a part of the embodiments of the present disclosure, not all the embodiments. It should be understood that terms used in the embodiments of the present disclosure are only used to explain specific embodiments of the present disclosure, rather than limiting the present disclosure. Based on the embodiments of the present disclosure, all other embodiments obtained by those of ordinary skill in the art without creative effects shall fall within the protection scope of the present disclosure.

It should be noted that, in the description of the present disclosure, directional or positional relationships indicated by terms such as "upper", "lower", "inner" and "outer" are based on directional or positional relationships shown in the accompanying drawings or directional or positional relationships for usual placement when a product of the present disclosure is used, are only intended to facilitate the description of the present disclosure and simplify the description, rather than indicating or implying that the appointed device or element has to be located in a specific direction or must be structured and operated in the specific direction so as not to be understood as limitations on the present disclosure.

In addition, in the following description, terms such as "first" and "second" are further used, are only used for distinguishing the description, and cannot be understood as indicating or implying the relative importance.

It should be noted that features in the embodiments of the present disclosure can be combined with each other without conflicts.

The present disclosure is preferably implemented in the form of software codes. Steps in the present disclosure are compiled into software codes to be installed in a computer with a calculation function, for example, are installed in a smartphone or a tablet computer in the form of the software codes.

Those of ordinary skill in the art can further realize that algorithm steps in all examples described in combination with the embodiments disclosed herein can be implemented by electronic hardware or a combination of computer software and the electronic hardware. Whether these functions are implemented by hardware or software depends on specific applications and design constraints of the technical solutions. Professional technicians can employ different methods to achieve the described functions in each specific application. However, such implementation should not be considered as departing from the scope of the present disclosure.

The present disclosure is implemented by installing a corresponding computer program in a computer with relevant hardware. The computer program may be stored in a computer-readable storage medium, and implements various required steps when executed by a processor, wherein the computer program includes a computer program code, and the computer program code can be in a source code form, an object code form, an executable file form or some intermediate forms, etc. The computer-readable storage medium may include any entity or device, a recording medium, a USB flash disk, a mobile hard disk, a diskette, a compact disc, a computer memory, an ROM (Read-Only Memory), an RAM (Random Access Memory), an electric carrier signal, a telecommunication signal, a software distribution medium, or the like capable of carrying the computer program code.

Main hardware of the computer in the present disclosure mainly includes the following main parts: a display screen 1, a central processing unit, an internal memory, a chip set, an I/O bus, I/O equipment, a power supply and relevant software.

The display screen 1 includes display screens of personal desktop computer and notebook computer. This type of display screen is connected to a main board of the computer, and the main board is connected to an input device, i.e., a mouse that inputs an instruction to the central processing unit on the main board.

The display screen 1 includes a touch screen. For the touch screen, capacitance is formed between a finger tip and the screen by using a current induction phenomenon of the finger tip of a user. A micro-current can be absorbed when a finger touches, and this current can make a current flow on electrodes of the touch screen, and a controller can calculate coordinates of a touch point by calculating the proportion of the current. At the same time, an area of contact between the finger tip and the touch screen can be calculated. In the following examples, the "surface" mentioned in the "50% of a contact surface of an input finger tip" refers to the area of contact between the finger tip and the touch screen, and the "50% of a contact surface" refers to a part occupying 50% of the total area of contact between the finger tip and the touch screen at present.

Example 1

A blood flow image signal in the present disclosure refers to a blood flow image acquired at a human blood vessel by ultrasound equipment, wherein it is necessary to collect and process ultrasound image information firstly, which can be realized with reference to an ultrasonoscope device in Chinese patent CN209751086U.

Referring to FIG. 1, in the present embodiment, the ultrasonoscope device includes an ultrasound transducer for emitting a scanning beam, a digital control processing chip for controlling the ultrasound transducer to emit the scanning beam and collect an echo signal, a portable control terminal for emitting a control instruction to the digital control processing chip and viewing a scanned image, as well as a transmitting-receiving multiplexing circuit, a transmitting-receiving switching circuit, a transmitting circuit, a receiving circuit, a USB interface circuit, a low-power module and an ultrasonoscope housing.

The transmitting-receiving switching circuit, the transmitting-receiving multiplexing circuit and the ultrasound transducer are sequentially connected in series. The transmitting circuit and the receiving circuit are respectively connected to the transmitting-receiving switching circuit. The ultrasound transducer, the digital control processing chip, the transmitting-receiving multiplexing circuit, the transmitting-receiving switching circuit, the transmitting circuit, the receiving circuit and the USB interface circuit are all packaged in the ultrasonoscope housing. The ultrasound transducer is located on a front end of the ultrasonoscope housing. A front end surface of the ultrasonoscope housing is a coupling plane. The USB interface circuit is located on a rear end of the ultrasonoscope housing.

The low-power module is internally provided with:
1. a digital power supply, which is configured to supply adaptive electrical energy to the digital control processing chip, the transmitting-receiving switching circuit, the transmitting circuit and the transmitting-receiving multiplexing circuit, is internally provided with a linear voltage regulator for protecting the voltage stability thereof, and is connected to the digital control processing chip, the transmitting-receiving switching circuit, the transmitting circuit and the transmitting-receiving multiplexing circuit respectively;
2. an analog power supply, which is configured to supply adaptive electrical energy to the transmitting-receiving multiplexing circuit and the receiving circuit, is internally provided with a linear voltage regulator for protecting the voltage stability thereof, and is connected to the transmitting-receiving multiplexing circuit and the receiving circuit respectively;
3. an adjustable high-voltage DC converter, which is configured to supply an adaptive high voltage to the transmitting circuit, and is connected to the transmitting circuit; and
4. an overcurrent protector, which is configured to limit the intensity of current supplied to the digital power supply, the analog power supply and the adjustable high-voltage DC converter, wherein the digital power supply, the analog power supply and the adjustable high-voltage DC converter are respectively connected to the USB interface circuit by the overcurrent protector.

The blood flow image acquired by the above-mentioned ultrasound equipment can be used as an image displayed on an interface in a color Doppler ultrasound spectrum mode in the present disclosure.

The interface in the color Doppler ultrasound spectrum mode in the present disclosure can generate instructions, and the instructions that are issued to the ultrasonoscope device via the USB interface circuit by a processor in the present disclosure to control circuits and all functional modules of the ultrasonoscope device, thereby controlling an ultrasound transducer probe of the ultrasonoscope device to acquire a desired signal. Therefore, it can be understood that the interface in the color Doppler ultrasound spectrum mode in the present disclosure controls the ultrasonoscope device, wherein operation for sampling tools on the interface is control on the ultrasonoscope device. Of course, the processor of the present disclosure, instead of a signal fed back by the ultrasonoscope device, is notified of performing certain processing. That is, whether the instructions generated on the interface in the color Doppler ultrasound spectrum mode in the present disclosure are specifically executed by the ultrasonoscope device serving as hardware or software in the processor depends on a processing workload and individual functions, part of work which can be processed by the ultrasonoscope device can also be delivered to the processor to be processed, and the work which is relatively difficult to process by the processor due to high workload can also be delivered to the ultrasonoscope device to be processed.

The portable control terminal shown in FIG. 1 is equipment which can be displayed on the interface in the color Doppler ultrasound spectrum mode in the present disclosure and is specifically a computer, a smartphone or a tablet computer installed with software capable of performing a method in the present disclosure.

Example 2

An interface 11 in a color Doppler ultrasound spectrum mode is generated on a display screen 1.

Figure 3:
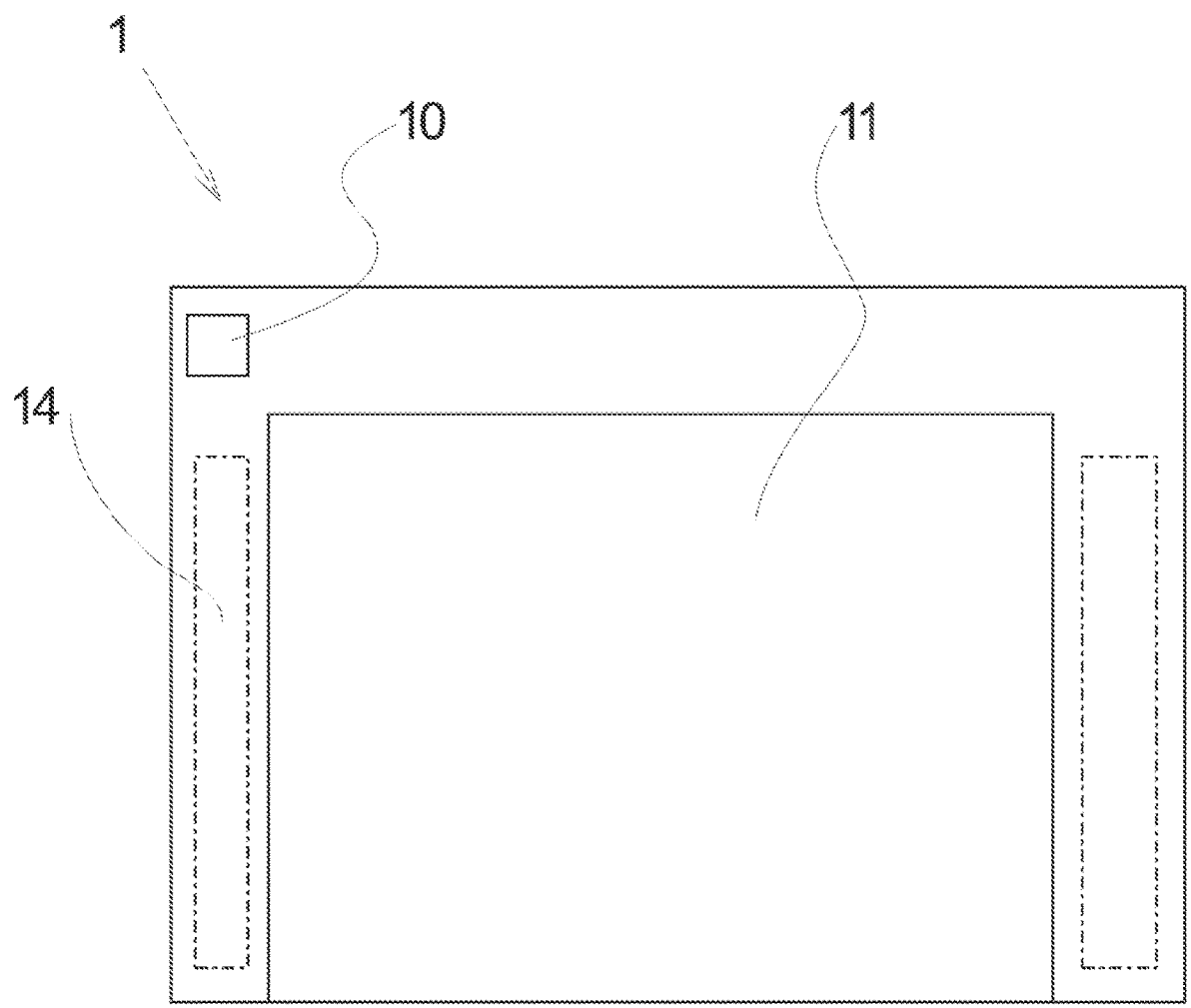
FIG. 3 is a schematic diagram of layout of an interface in a color Doppler ultrasound spectrum mode in the present disclosure.

Referring to FIG. 3, the interface in the color Doppler ultrasound spectrum mode is provided with virtual buttons for other functional regions 14, such as a button for starting or stopping an ultrasound interface and a button for exiting the interface in the color Doppler ultrasound spectrum mode. Particularly, the interface in the color Doppler ultrasound spectrum mode is provided with a first button 10 for entering a blood flow spectrum display stage from a sampling preparation stage. Various parameters are set at the sampling preparation stage. After sampling work is adjusted, the first button 10 is clicked, and thus, the interface is changed from an interface 2 at a sampling preparation stage to an interface 3 at a blood flow spectrum display stage.

During specific execution, the interface in the color Doppler ultrasound spectrum mode in the present disclosure has two modes, wherein one of the modes is a sampling preparation mode, and the other mode is a blood flow spectrum display mode. These two modes are performed in stages. During normal work, in order to obtain blood flow spectrum images, it is necessary to perform operations, including adjustment of sampling tools, on the interface 2 at the sampling preparation stage firstly, and then to enter the interface 3 at the blood flow spectrum display stage after the adjustment is completed, which is therefore referred to as a sampling preparation stage and a blood flow spectrum display stage in the present disclosure. It can be considered that various parameters including sampling ranges, sampling directions and pulse repetition frequencies are mainly preset at the sampling preparation stage, and output is performed according to the preset parameters at the blood flow spectrum display stage.

Figure 4:
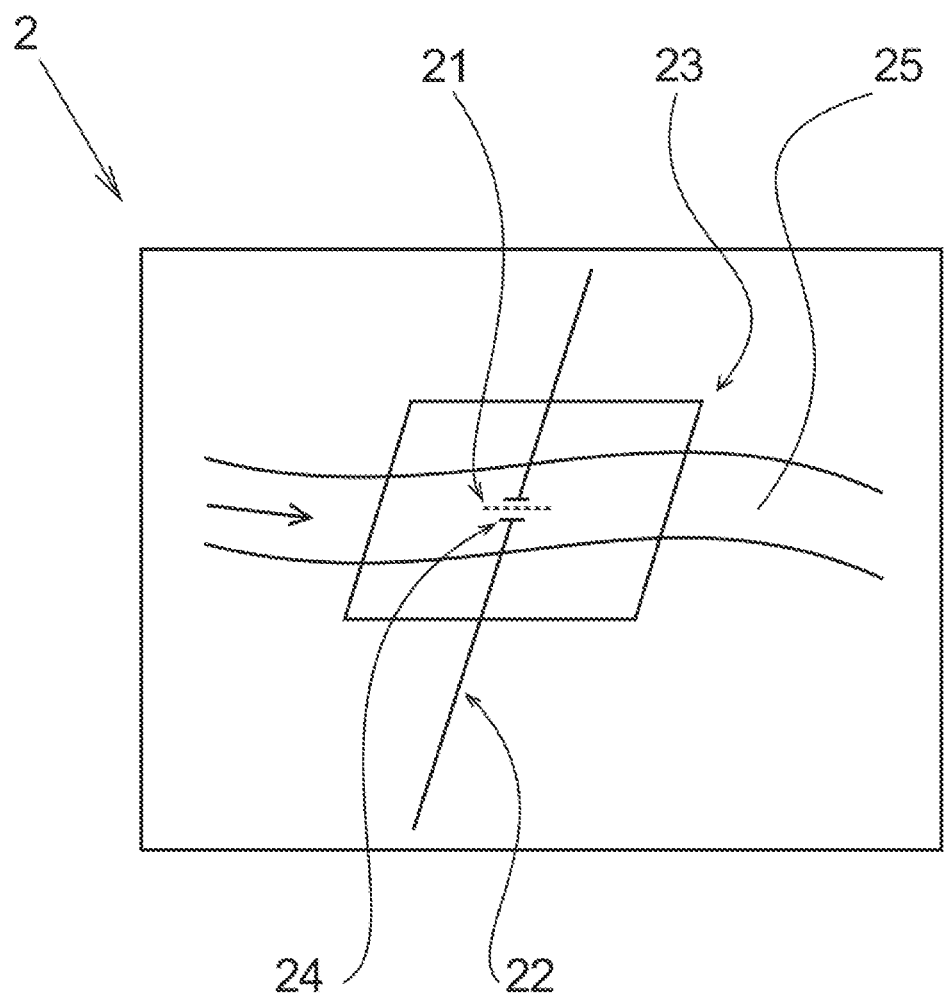
FIG. 4 is a schematic diagram of an interface at a sampling preparation stage in the present disclosure.

Therefore, referring to FIG. 4, at the sampling preparation stage, there is a blood flow ultrasound image display region on the interface, and the entire interface is fully occupied by blood flow ultrasound images, and displays vascular ultrasound images and a plurality of sampling tools for sampling the blood flow ultrasound images in both range and direction, wherein the sampling tools overlap with the blood flow ultrasound images. The sampling tools are some high-brightness lines or line frames, which are more obvious on the vascular ultrasound images and easy to recognize. Specifically, the sampling tools are some high-brightness color lines or line frames.

The sampling tools will be specifically described as follows.

(1) A sampling frame 23: The sampling frame is located in the middle of the blood flow ultrasound image display region and is specifically in a shape of a parallelogram. A color region in the sampling frame is configured to mark blood vessel color Doppler ultrasound images. A segment of a blood vessel 25 passes through the sampling frame from left to right generally, and is displayed in color in the sampling frame, which is beneficial to the visual observation for basic situations of the blood vessel 25.

(2) A sampling volume tool 24: The sampling volume tool is located in the middle of the sampling frame 23, is formed by a pair of horizontally-disposed shorter parallel lines, and is configured to mark an intravascular sampling volume, wherein a calculated volume refers to a volume of a blood flow between the two parallel lines for a sampling volume. During sampling, in order to determine a position required to be sampled, the sampling volume tool needs to move on a longitudinal section in the blood vessel, and moves on the blood vessel 25 when the position required to be sampled is on the blood flow ultrasound images. A specific movement position is determined as required by a doctor.

(3) A blood flow direction tool 21: The blood flow direction tool is a line segment located between the parallel lines for the sampling volume, is a first line segment longer than the parallel lines forming the sampling volume tool, has two ends extending out from gaps in two ends of the sampling volume tool (the sampling volume tool is a pair of horizontal parallel lines, and two ends thereof are similar to gaps), and is configured to mark a blood flow direction. During work, the blood flow direction tool is parallel to the blood flow direction, and is approximately parallel to a blood vessel wall. Adjustment for the blood flow direction tool means changing the marking for the blood flow direction, which will affect a blood flow spectrum output result. It is possible that the blood vessel on the blood flow ultrasound images is not in the same direction as the blood flow direction tool, and a deflection angle is formed therebetween. At the moment, the user needs to perform operation to adjust the blood flow direction tool, making the blood flow direction tool parallel to the blood flow direction.

(4) A blood flow spectrum sampling line 22: The blood flow spectrum sampling line is a line segment (second line segment) longitudinally passing through the sampling frame. During ultrasound spectrum work, a cross section in the blood vessel is sampled, the blood flow spectrum sampling line marks the specific sampling position on the section of the blood vessel, and movement of the blood flow spectrum sampling line means movement of the section of the blood vessel.

At the sampling preparation stage, a plurality of sampling instruction receiving regions are generated on a first position where a part of pixels of the sampling tools are located. Specifically, for the above-mentioned sampling tools, in order to more conveniently and intuitively operate each sampling tool, the sampling instruction receiving regions are generated on the sampling tools. Specifically, a first instruction receiving region 91 is disposed at a position where pixels on two ends of the first line segment forming the blood flow direction tool and regions near the pixels on the two ends are located; and an instruction received by the first instruction receiving region is configured to control the blood flow direction tool to deflect and specifically control the first line segment to rotate about the center, so that the first line segment is manually controlled to be parallel to the blood vessel wall or the blood flow direction, and thus, the calculated blood flow spectrum parameter result is more accurate.

Figure 5A:
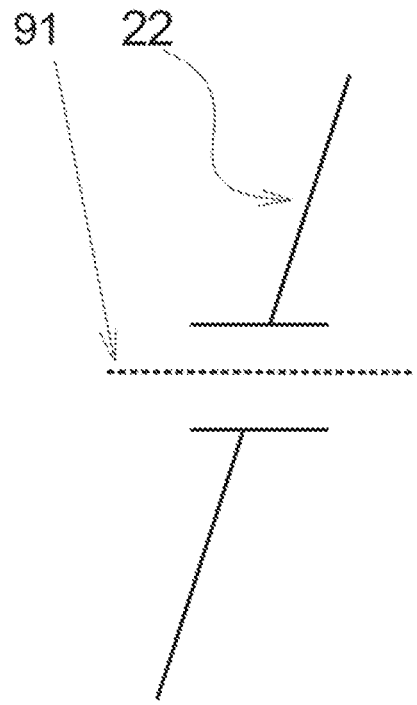
FIGS. 5A-5D are a schematic diagram of a first instruction receiving region and an instruction input into the first instruction receiving region in the present disclosure.
Figure 5B:
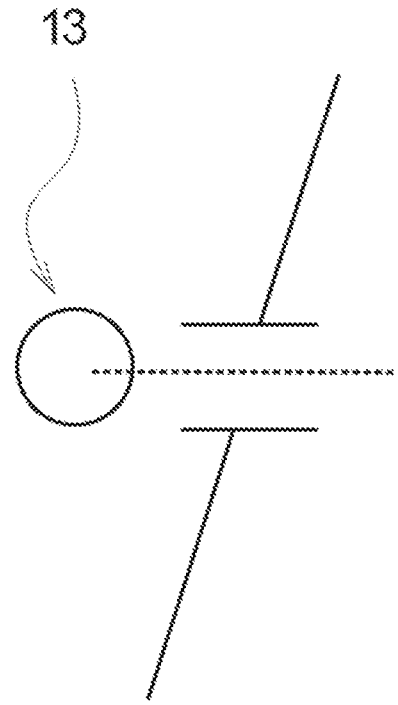

Referring to FIG. 5A, in one example, the first instruction receiving region includes the pixels on the two ends of the first line segment, and the first instruction receiving region follows the pixels on the two ends of the first line segment regardless of movement of the pixels to any position on the interface. Therefore, in one of examples, if any one of pixels on the two ends of the first line segment is covered by a finger tip contact surface 13 for user input, it is considered that the input is performed in the first instruction receiving region (referring to FIG. 5B). In one of examples, in the case of input by a mouse, if any one of the pixels on the two ends of the first line segment is touched by a mouse pointer, it is considered that the input is performed in the first instruction receiving region.

Figure 5C:
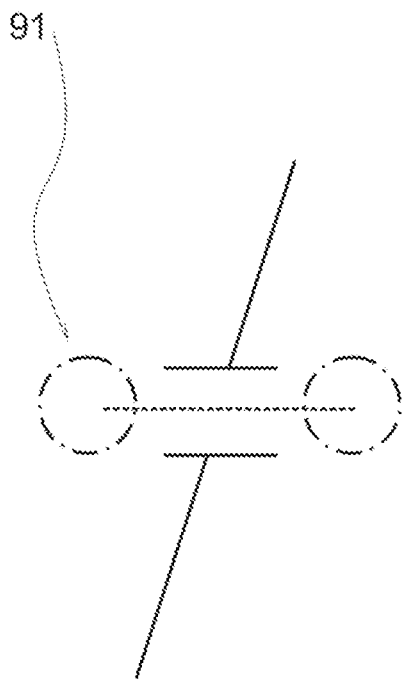
Figure 5D:
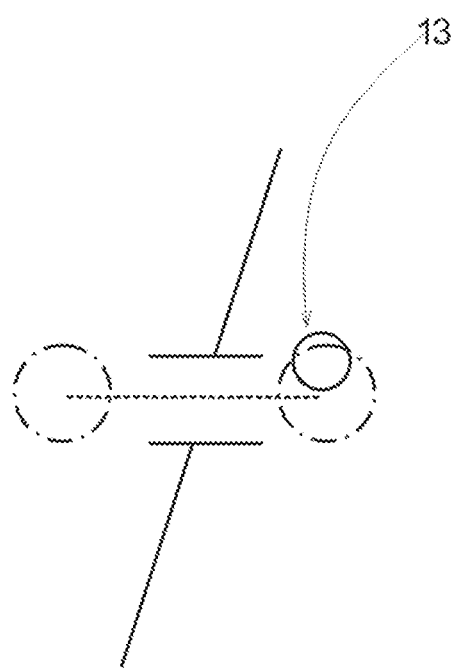

Referring to FIG. 5C, in another example, the first instruction receiving region includes the pixels on the two ends of the first line segment and peripheral regions of the pixels on the two ends of the first line segment, and the first instruction receiving region (including the peripheral regions) follows the pixels on the two ends of the first line segment regardless of movement of the pixels to any position on the interface. After the first line segment rotates, the instruction region also follows the first line segment to move, and a position which originally belongs to the first instruction receiving region is no longer the first instruction receiving region. When the first line segment moves to the current position, the current position which does not belong to the first instruction receiving region originally falls within the first instruction receiving region now. Sizes of the peripheral regions are determined according to the size of the screen, which are not limited. For example, it can be set that pixels within the pixel range of 100 on the two ends of the first line segment all belong to the first instruction receiving region. Referring to FIG. 5D, if any one of the pixels of the first instruction receiving region is covered by the finger tip contact surface 13 for user input, it is considered that the input is performed in the first instruction receiving region. Or if the pixels of the first instruction receiving region are covered by 50% or above of the finger tip contact surface for user input, it is considered that an instruction is given in the first instruction receiving region. In one of examples, in the case of input by the mouse, if any one of pixels of the first instruction receiving region is touched by the mouse pointer, it is considered that an instruction is given in the first instruction receiving region.

When touch input via the finger tip is employed, the touch screen receives changes in a finger tip touch signal of the user to form an instruction, which requires an accurate position where the user inputs the instruction. However, the area of the finger tip of the user is relatively large, which causes a difficulty in precisely ensuring that a coverage range is on and only on the two ends of the first line segment, or a difficulty in moving the mouse pointer to the accurate position. This problem is avoided in the above-mentioned two examples.

After the first instruction receiving region is determined, a plurality of sampling instruction receiving regions are provided at other positions excluding the first instruction receiving region, and sampling ranges of the sampling tools and pulse repetition frequencies can be changed in these sampling instruction receiving regions.

Figure 6A:
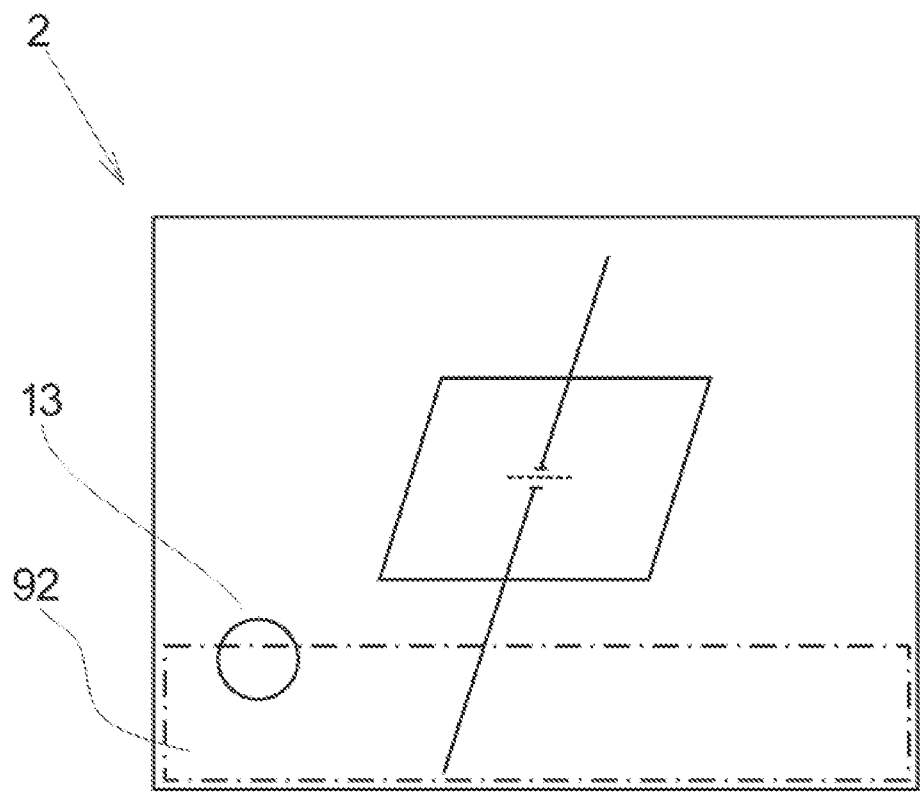
FIGS. 6A-6B are a schematic diagram of a second instruction receiving region and an instruction input into the second instruction receiving region in the present disclosure.
Figure 6B:
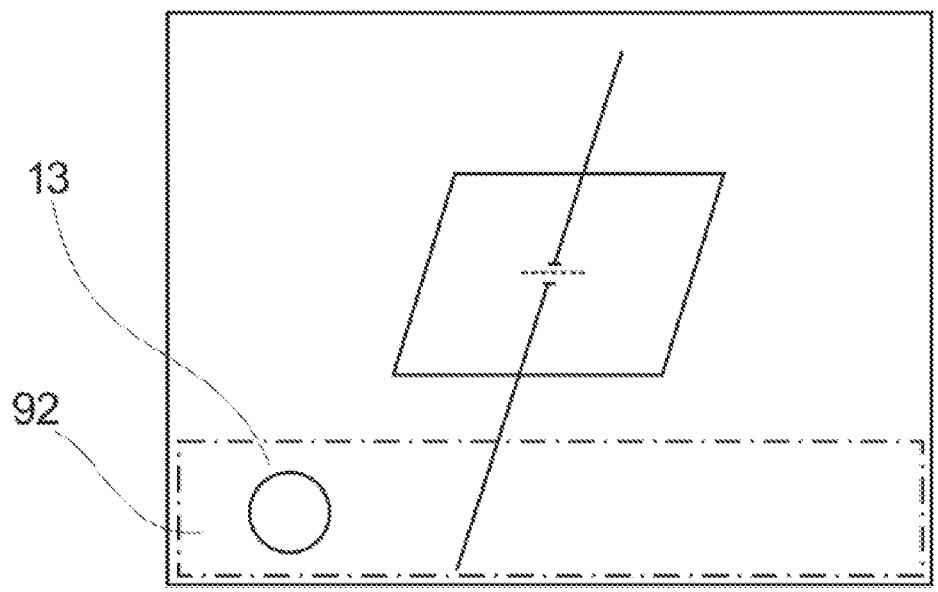
Figure 7A:
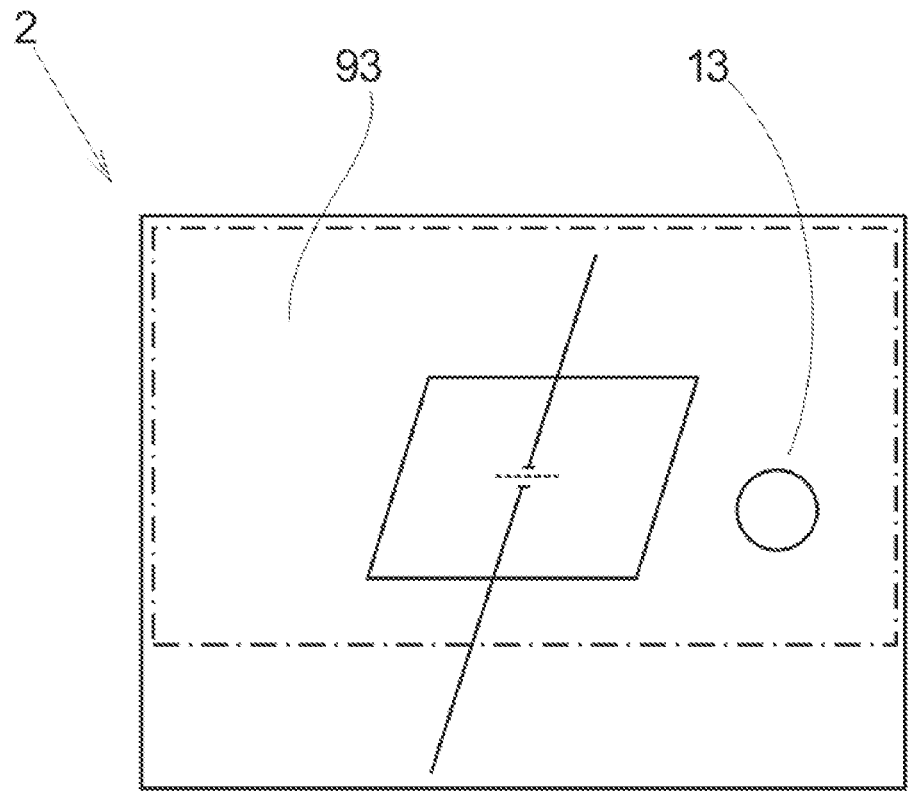
FIGS. 7A-7B are a schematic diagram of a third instruction receiving region and an instruction input into the third instruction receiving region in the present disclosure.

Referring to FIG. 6A, a part, occupying ⅓ of the area of the interface, on a lower part of the interface is a second instruction receiving region 92, wherein a lower end of the sampling line passes through this region. Referring to FIGS. 6A and 6B, if pixels of the second instruction receiving region are covered by 50% or above of the finger tip contact surface for user input, it is considered that an instruction is given in the second instruction receiving region and is used for moving a sampling position of the blood flow spectrum sampling line on the section of the blood vessel. If pixels of the second instruction receiving region are covered by 50% or above of the finger tip contact surface for user input, it is considered that an instruction is given in the second instruction receiving region. In one of example, in the case of input by the mouse, if any one of pixels of the second instruction receiving region is touched by the mouse pointer, it is considered that an instruction is given in the second instruction receiving region Referring to FIG. 7A, a third instruction receiving region 93 is located on an upper part of the interface and is a part occupying ⅔ of the area of the interface. The second instruction receiving region is correspondingly divided, and occupies ⅓ of the area on the lower part of the interface, and the third instruction receiving region occupies ⅔ of the area on the upper part of the interface, wherein ⅓ and ⅔ described herein are not definite, which can also be adjusted optionally. For example, the second instruction receiving region and the third instruction receiving region can be adjusted to occupy ½ of the area of the interface, respectively. It can be seen from FIGS. 7A and 7B that the third instruction receiving region is a part excluding the part where the first instruction receiving region is located. The first instruction receiving region is actually enclosed by the third instruction receiving region. During operation, the first instruction receiving region and the third instruction receiving region may interact with each other, for example, the user originally intends to operate the first instruction receiving region, but most of the input touch surface overlies the third instruction receiving region. Therefore, in order to avoid such an event, the area of the first instruction receiving region needs to be increased as much as possible, so that when the user intends to input in the first instruction receiving region, it is easier to cover the finger tip contact surface to the pixels of the first instruction receiving region, and when the user intends to input in the third instruction receiving region, the first instruction receiving region is kept away as much as possible, avoiding touching the first instruction receiving region by mistake.

If the third instruction receiving region is covered by a part (even if most) of the finger tip contact surface of the finger tip for user input, and the pixels of the first instruction receiving region are covered by the other part (even if a small part) of the finger tip contact surface, it should be also considered that the instruction is given in the first instruction receiving region, instead of the third instruction receiving region. Therefore, it is considered that the instruction given in the third instruction receiving region when in two situations as follows.

Figure 7B:
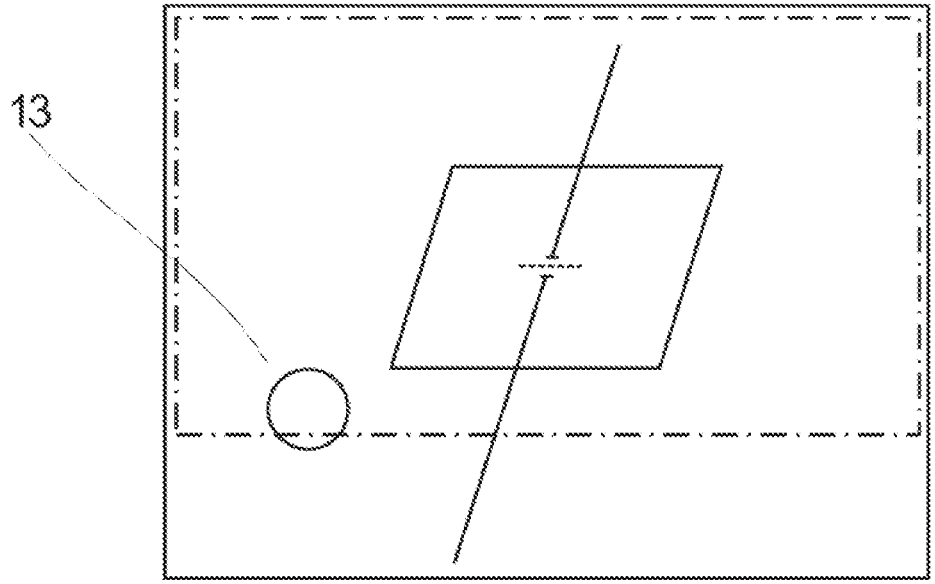

1. Referring to FIG. 7B, if the pixels of the third instruction receiving region are covered by 50% or above of the finger tip contact surface 13 for user input, and the pixels of the second instruction receiving region are covered by the other part of finger tip contact surface, it is considered that the instruction is given in the third instruction receiving region.

2. If the third instruction receiving region is covered by the entire finger tip contact surface of the finger tip for user input, it is considered that the instruction is given in the third instruction receiving region.

In another embodiment, it is not convenient to excessively emphasize the priority of the first instruction receiving region and define that the instruction is given in the first instruction receiving region only when the pixels of the first instruction receiving region are covered by 50% or above of the finger tip contact surface for user input. Therefore, it is also considered that the instruction is given in the third instruction receiving region when in a third situation as follows: if the third instruction receiving region is covered by 50% or above of the finger tip contact surface for user input in any condition, it is considered that the instruction is given in the third instruction receiving region.

In one of examples, in the case of input by the mouse, if any one of the pixels of the third instruction receiving region is touched by the mouse pointer, it is considered that the instruction is given in the third instruction receiving region.

The instruction given in the third instruction receiving region is used for moving a sampling position of the sampling volume tool.

Figure 8:
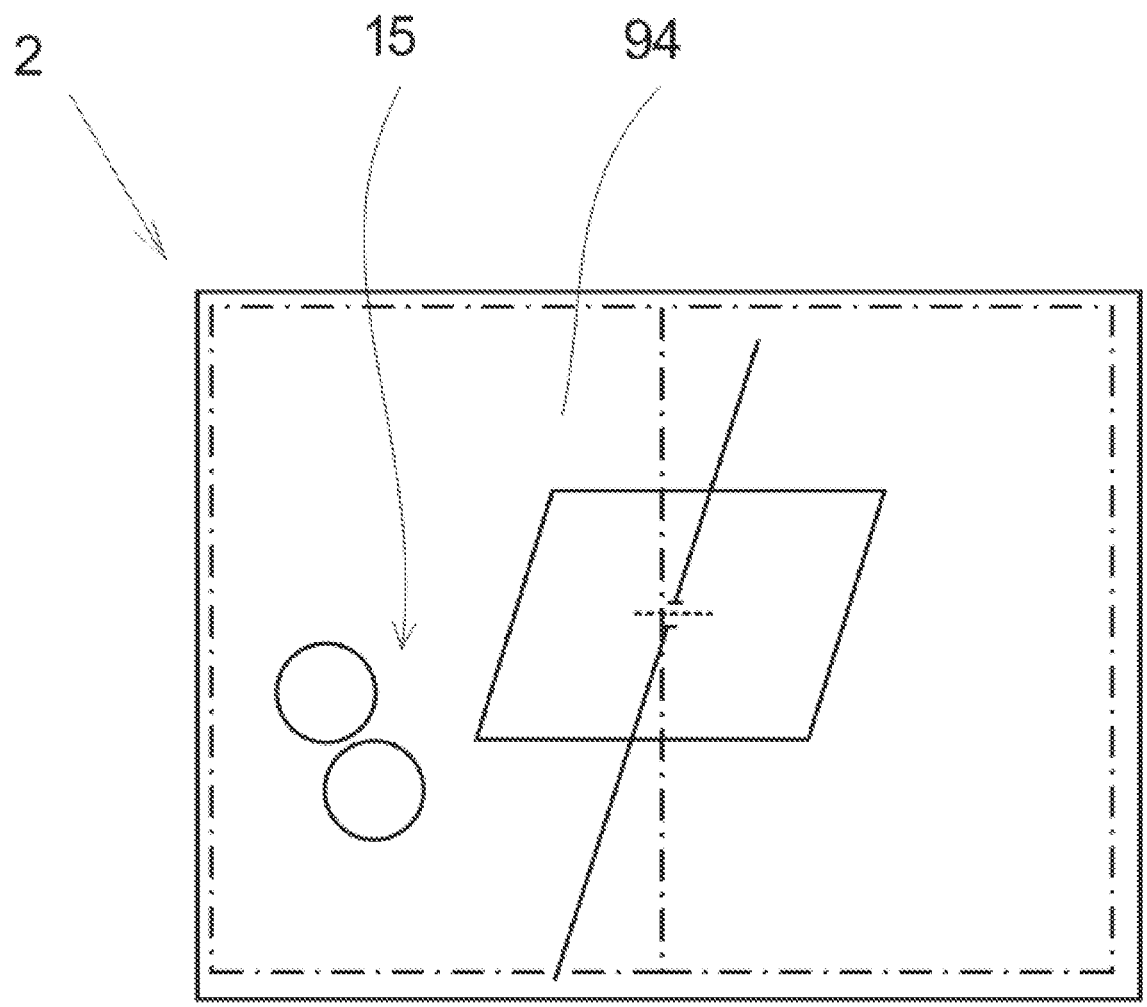
FIG. 8 is a schematic diagram of a fourth instruction receiving region and an instruction input into the fourth instruction receiving region in the present disclosure.

Referring to FIG. 8, a fourth instruction receiving region 94 for changing a pulse repetition frequency value or a sampling volume is disposed at any position on a left part or a right part of the interface.

In one of examples, a fourth instruction receiving region is disposed on the left part occupying ½ of the area of the interface, and an instruction input into this part is used for changing the sampling volume.

In one of examples, a fourth instruction receiving region is disposed at the right part occupying ½ of the area of the interface, and an instruction input into this part is used for changing the pulse repetition frequency value.

In one of examples, one of the fourth instruction receiving region for changing the sampling volume and the fourth instruction receiving region for changing the pulse repetition frequency value can be optionally disposed on any one of the left part and the right part, and the other one of the fourth instruction receiving region is disposed on the other one of the left part and the right part. Moreover, the left part and the right part of the interface are not necessarily divided in half (each occupies ½ of the area of the interface), and the region can be optionally divided.

In a preferred example, a functional region for changing the pulse repetition frequency value in the fourth instruction receiving region is disposed on the left part occupying ½ of the area of the interface, and an instruction input into this part is used for changing the pulse repetition frequency value. A functional region for changing the sampling volume in the fourth instruction receiving region is disposed on the right part occupying ½ of the area of the interface, and an instruction input into this part is used for changing the sampling volume.

The fourth instruction receiving region conflicts with the first instruction receiving region, the second instruction receiving region and the third instruction receiving region in position, and therefore, recognizing the instruction by mistake can be avoided by virtue of the number of input touch points, thereby avoiding confusion. In one of examples, the instruction is recognized to be given in the fourth instruction receiving region under multi-point touch 15. The multi-point touch refers to that touch with other number of touch points excluding the single-point touch, for example, inputs from two or more touch points received in the fourth instruction receiving region are considered to be multi-point touch.

There is still a situation that, in the multi-point touch, the coverage of a part of the finger tip contact surface in inaccurate, for example, one of finger tip contact surfaces is located on a boundary of the left part and the right part, or one of the finger tip contact surfaces is located on the left part, and the other one of the contact surface is located on the right part, such a situation can be recognized as invalid input, and no response is triggered; or preferably, the instruction is considered to be an instruction for changing the sampling volume. The input by the mouse pointer is not applicable to the fourth instruction receiving region.

On the interface in the color Doppler ultrasound spectrum mode, the first button 10 is clicked after the sampling work is adjusted, and thus, the interface enters a blood flow spectrum display stage from a sampling preparation stage and is also switched to the interface 11 in the color Doppler ultrasound spectrum mode, a calculated result, i.e., a blood flow spectrum image, is output according to parameters preset at the sampling preparation stage.

The interface in the color Doppler ultrasound spectrum mode 11 is provided with a blood flow ultrasound image display region 31 and a blood flow spectrum image region side by side. One of side-by-side manners is left/right arrangement on the interface, wherein the blood flow ultrasound image display region is located on the left, and the blood flow spectrum image region is located on the right. However, display in such a manner is not beneficial to viewing.

Figure 9:
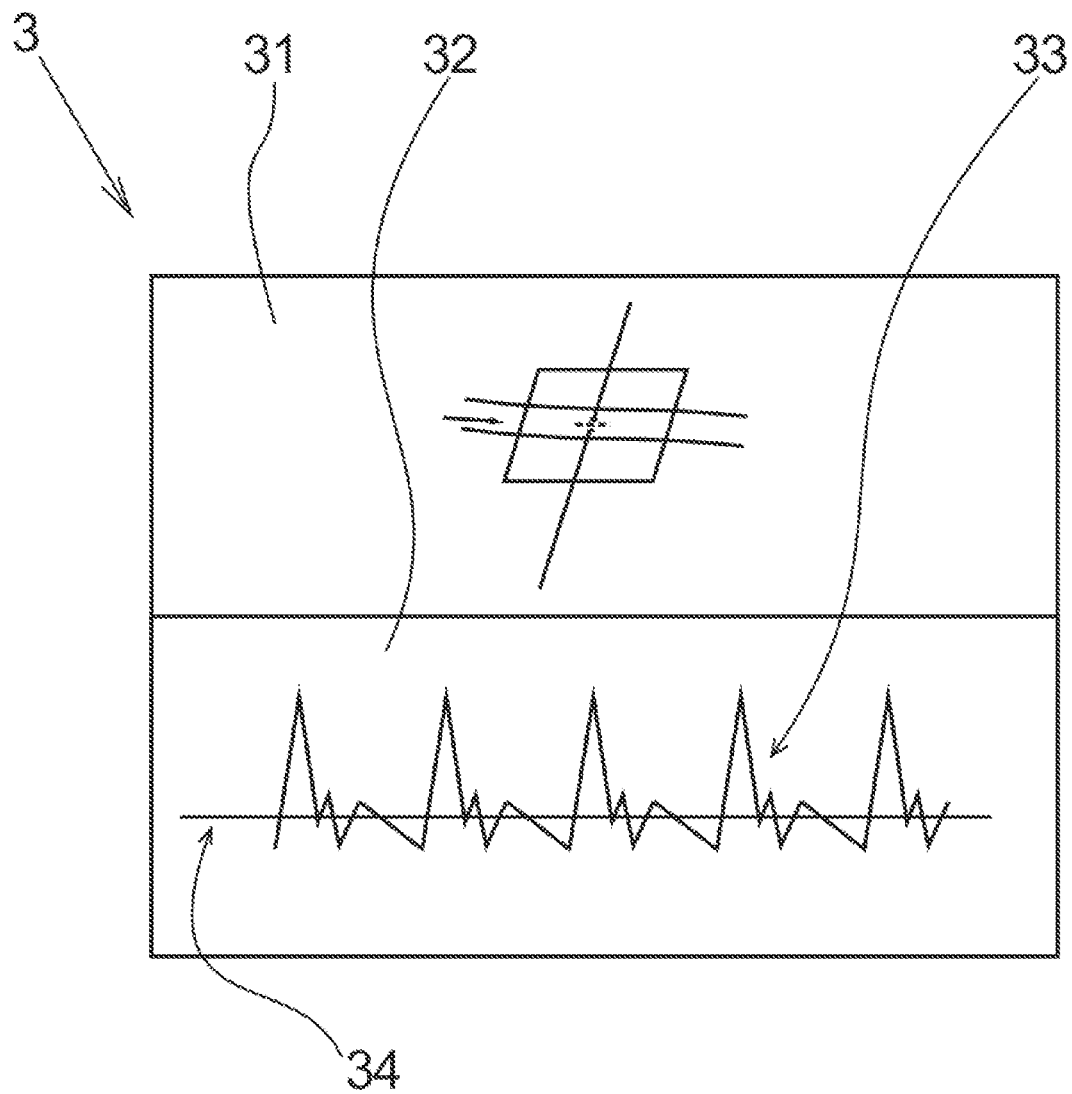
FIG. 9 is a schematic diagram of an interface at a blood flow spectrum display stage in the present disclosure.

Referring to FIG. 9, in a preferred example, up/down arrangement is employed on the interface, wherein the blood flow ultrasound image display region is located on the upper part, and the blood flow spectrum image region is located on the lower part. Such a manner is beneficial to viewing and can display more image information.

In this example, all the blood flow ultrasound images occupy the blood flow ultrasound image display region. Meanwhile, there are also a plurality sampling tools for sampling the blood flow ultrasound images in range and direction in this region, and the sampling tools overlap with the blood flow ultrasound images. The sampling tools are some high-brightness lines or line frames that are displayed on the blood vessel ultrasound images and easy to recognize. Specifically, the sampling tools are some high-brightness color lines or line frames and include a sampling frame 23, a sampling volume tool 24, a blood flow direction tool 21 and a blood flow spectrum sampling line 22. However, different from those at the sampling preparation stage, the sampling tools at the blood flow spectrum display stage are no longer operated and adjusted, all the instruction receiving regions at the sampling preparation stage (within the interface) are closed to no longer receive the instructions.

Blood flow spectrum images and a blood flow spectrum baseline 34 passing through the blood flow spectrum images are transversely displayed from left to right in the blood flow spectrum image region on the lower part, and the position of the baseline can be adjusted up and down. The baseline 34 has the effects as follows: Spectra of the blood flow spectrum images are divided in two directions including a positive direction and a negative direction. Starting from the baseline, a part located above the baseline is in the positive direction, a part located below the baseline is in the negative direction, and the position where the baseline is located is zero. Therefore, the up-and-down adjustment for the baseline actually means adjustment for a range displayed in the positive direction and the negative direction. For example, if the part located above is in the positive direction and the part located below is in the negative direction, when the baseline is adjusted upwards, the part in the negative direction is more displayed, and then, the part in the positive direction is reduced. However, during actual ultrasound output of the images, the images in the positive direction and the negative direction are not necessarily have the same height. Sometimes, the images are concentrated in the negative direction, moreover, the image in the negative direction has a greater height, and the image in the positive direction has very small height, so that the part in the negative direction is required to be more displayed. Or else, the displayed image will have a reflection, resulting in incorrect image displaying. Therefore, the baseline needs to be adjusted up and down manually.

At the blood flow spectrum display stage, the sampling instruction receiving regions are required to be closed synchronously. The original first to fourth instruction receiving regions exit to no longer receive user input.

Moreover, a blood flow spectrum image control instruction region is generated in each of the blood flow ultrasound image display region and the blood flow spectrum image region.

For control on the blood flow spectrum images, it is required to control the following three parameters: ultrasound signal gain adjustment, a position of the baseline, and a spectrum speed.

Figure 10:
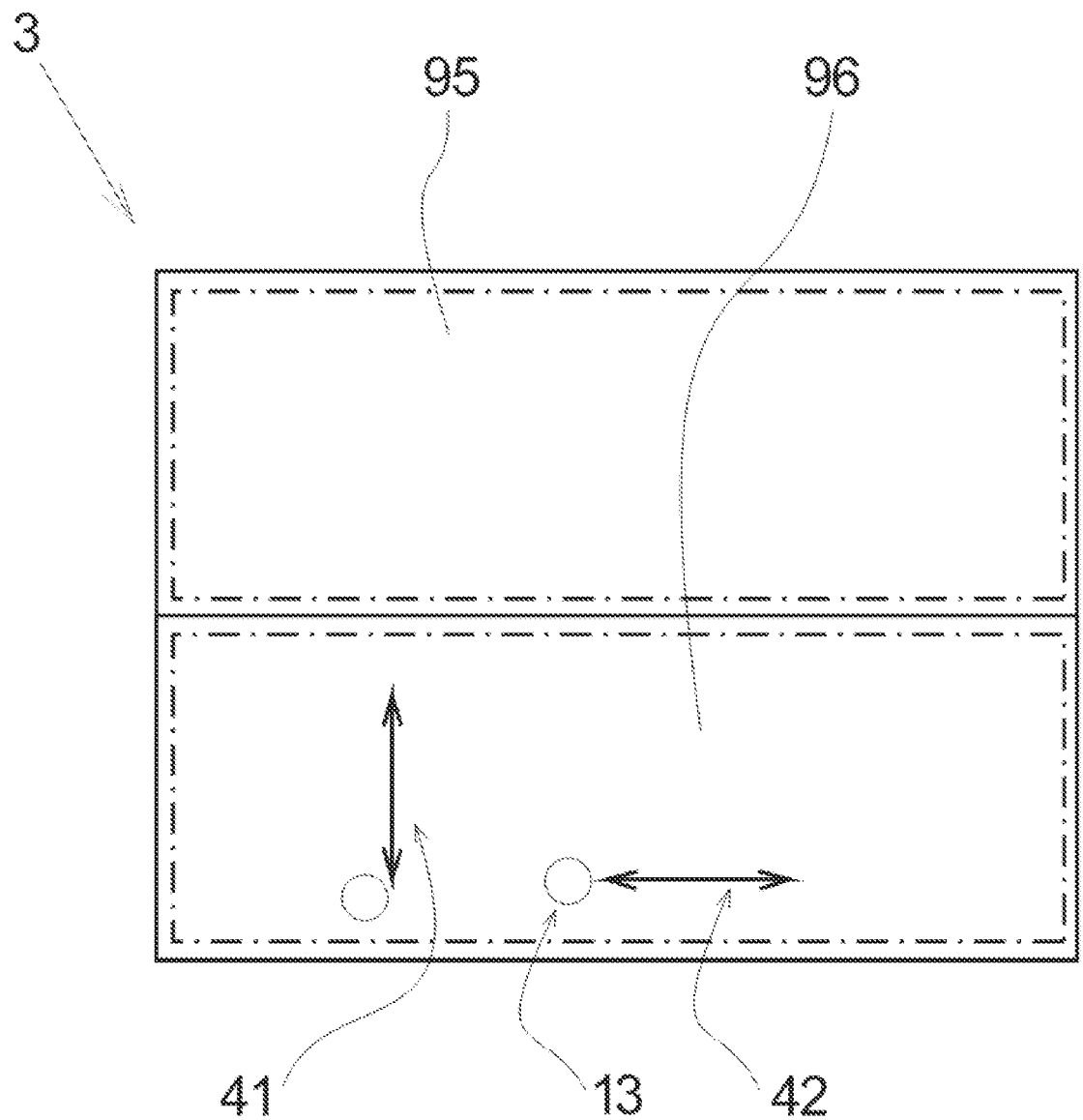
FIG. 10 is a schematic diagram of a blood flow spectrum image control instruction region and an instruction input into the blood flow spectrum image control instruction region in the present disclosure.

Therefore, referring to FIG. 10, an ultrasound signal gain adjustment instruction receiving region (hereinafter referred to as: a fifth instruction receiving region 95) is generated in the blood flow ultrasound image display region, and a baseline position and spectrum speed adjustment instruction receiving region (hereinafter referred to as: a sixth instruction receiving region 96) is generated in the blood flow spectrum image region.

A boundary between the blood flow ultrasound image display region and the blood flow spectrum image region is used as a boundary between the fifth instruction receiving region and the sixth instruction receiving region. The fifth instruction receiving region is located on the upper part, and the sixth instruction receiving region is located on the lower part. If pixels of the fifth instruction receiving region are covered by 50% or above of the finger tip contact surface 13 for user input, it is considered that the instruction is given in the fifth instruction receiving region and is used for adjusting an ultrasound signal gain. In one of examples, in the case of input by the mouse, any one of pixels of the fifth instruction receiving region is touched by the mouse pointer, it is considered that the instruction is given in the fifth instruction receiving region.

If pixels of the sixth instruction receiving region are covered by 50% or above of the finger tip contact surface for user input, it is considered that the instruction is given in the sixth instruction receiving region and is used for adjusting the position of the baseline or the spectrum speed. However, whether to adjust the position of the baseline or the spectrum speed is determined by the number of touch points shown in other examples. By adjusting the spectrum speed, a distance between spectrum waveforms can be widened, and a distance from a peak to a valley can be widened, thereby avoiding excessively intensive spectrum waveforms, and lowering the difficulty in recognition, observation and calculation. In one of examples, in the case of input by the mouse, pixels of the fifth instruction receiving region are touched by the mouse pointer, it is considered that the instruction is given in the sixth instruction receiving region.

Example 3 shows an operation method for an interface in a color Doppler ultrasound spectrum mode.

The interface in the color Doppler ultrasound spectrum mode in the present disclosure is displayed using the display screen 1, and interacts with a user by the display screen 1, and an instruction is input in manner of sliding input of the user on the interface, and specifically, in manner of finger touch or sliding of the mouse pointer on the interface in the color Doppler ultrasound spectrum mode.

In the case of finger touch, there are different numbers of touch points, including single-point touch and multi-point touch 15. The single-point touch means that coordinates of a touch point received by the display screen 1 result from a single-finger operation from the user; and the multi-point touch 15 means that coordinates of one or more touch points received by a touch display result from the two-finger or multi-finger operation from the user.

Mouse pointer sliding is equivalent to the single-point touch. When a mouse is operated, an action of dragging the mouse is adopted, that is, after the mouse pointer is moved to the corresponding instruction receiving region, a left button of the mouse is pressed, subsequently, the pointer is moved to a required distance, and then, the left button of the mouse is released. Single-point touch instructions in the first to third instruction receiving regions as well as the fifth and sixth instruction receiving regions described in all examples of the present disclosure and particularly the following examples are understood as finger tip touch of a single finger, which may be equivalent to the description of mouse pointer sliding. In order to avoid repetition, an example that an instruction is input by mouse pointer sliding will not be separately described. The example that the instruction is input by mouse pointer sliding may be derived unanimously as long as the single-point touch instructions in the first to third instruction receiving regions as well as the fifth and sixth instruction receiving regions are all understood as the finger tip touch of the single finger, which is understood as single-finger touch. The instruction input by mouse pointer sliding is not applicable to the fourth instruction receiving region.

Sliding input described herein includes a sliding input trajectory.

Figure 11:
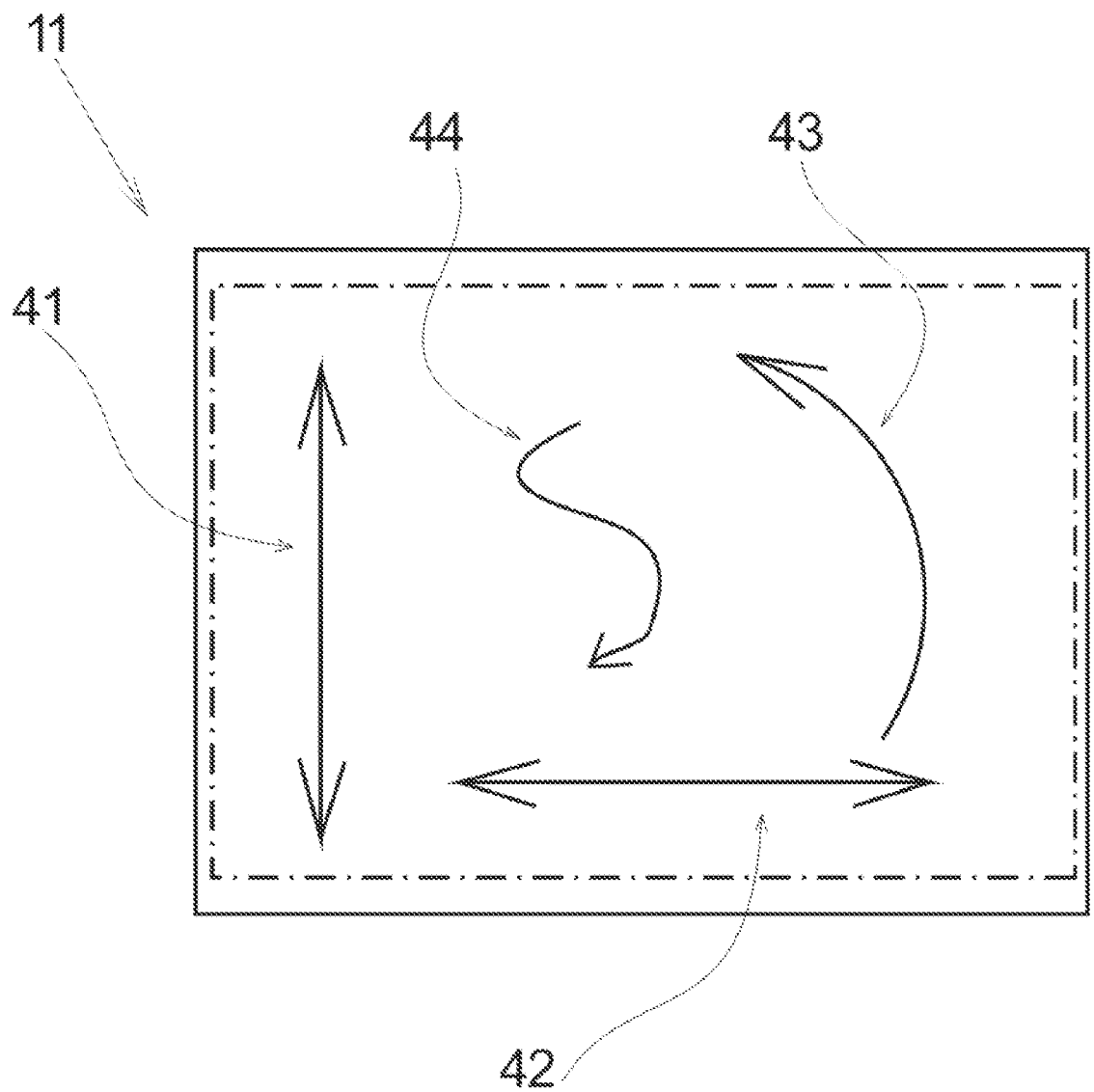
FIG. 11 is a schematic diagram of a sliding input trajectory.

Referring to FIG. 11, the trajectory refers to a process that a finger tip of a user continuously passes by a pixel row or a pixel column on the display screen 1, and the movement trajectory is in a first direction 41, a second direction 42, a third direction 43 and a fourth direction 44.

The first direction 41 is a direction of round-trip movement approximately parallel to the pixel column in the interface, that is, it is a process of approximately moving downwards from the upside of the display screen 1 and a process of approximately moving upwards from the downside of the display screen.

The second direction 42 is a direction of round-trip movement approximately parallel to the pixel row in the interface, that is, it is a process of approximately moving rightwards from the right of the display screen and a process of approximately moving towards the upper left part from the right of the display screen.

The third direction 43 is a direction of approximate arc movement around the center of the interface. Herein, the interface is required to be taken as a center, and of course, the center of a tool operated currently can also be as a center. Two tools required to be operated in the third direction are also located in the middle of the interface, and therefore, taking the interface as a center means taking the center of a called tool as a center.

The fourth direction 44 is a direction of an irregular curved movement on the display screen.

Figure 2:
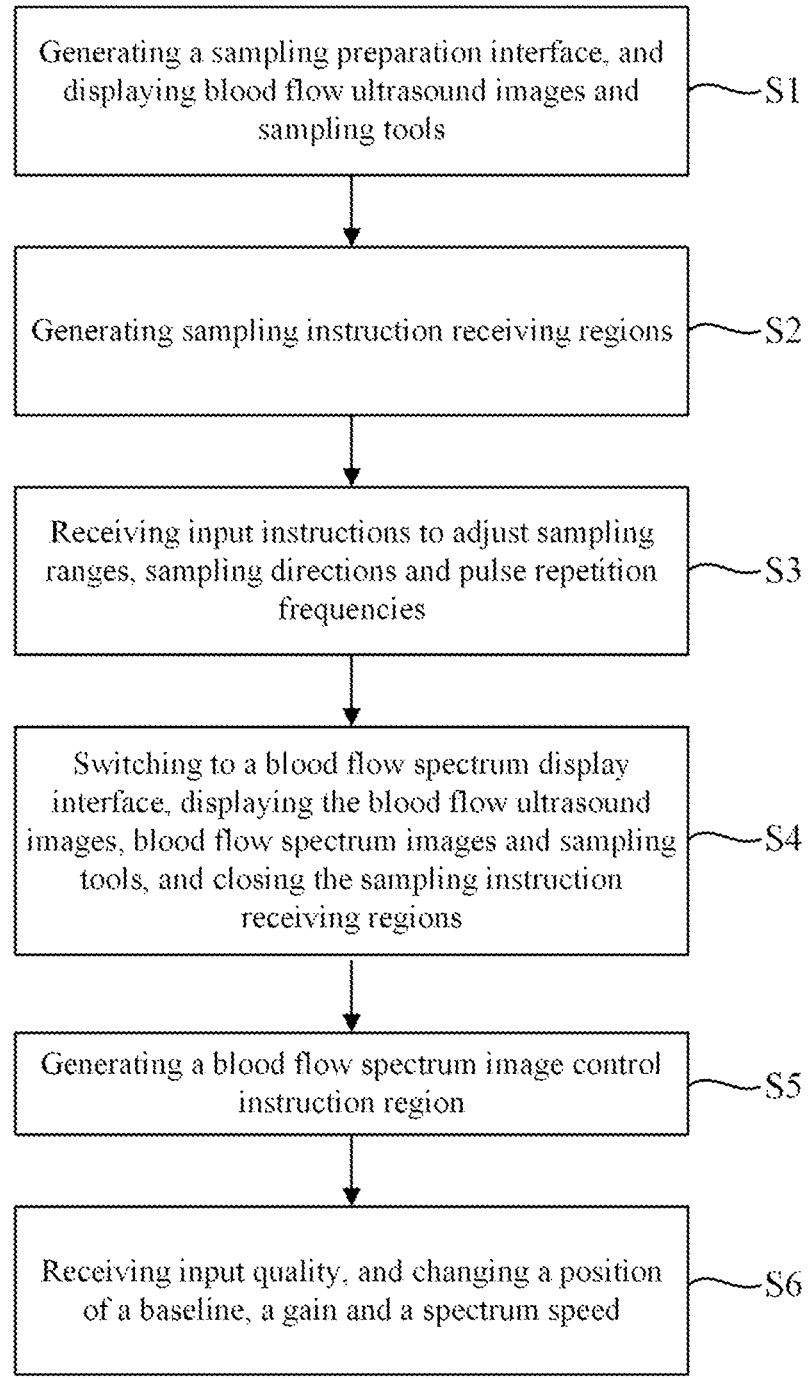
FIG. 2 is a process chart of an operation method for an interface in a color Doppler ultrasound spectrum mode in the present disclosure.

Referring to FIG. 2, the operation method for the interface in the color Doppler ultrasound spectrum mode is described as follows.

S1: When a color Doppler ultrasound spectrum mode is used, firstly, the interface in the color Doppler ultrasound spectrum mode is presented, contents of the interface refer to those in example 2, an interface 2 at a sampling preparation stage is generated on the touch screen, and blood flow ultrasound images and sampling tools are displayed to a user in the interface.

S2: Sampling instruction receiving regions are generated.

S3: Instructions input by the user in the sampling instruction receiving regions are received, and sampling ranges, sampling directions and pulse repetition frequencies of the sampling tools are adjusted according to the instructions. Specific steps are described as follows:

(1) When a single-point touch instruction from a user in a first instruction receiving region 91 is received, a blood flow direction tool is called. During instruction input, the blood flow direction tool rotatably changes, so that the input habit of the user may also approximately rotatably changes along with a first line segment, and thus, a movement trajectory of touch is in a third direction. The first instruction receiving region 91 is located on a position where pixels on two ends of the first line segment forming the blood flow direction tool and regions near the pixels on the two ends are located. If a finger tip of the user touches this region, it is considered that the blood flow direction tool is called, and an instruction for adjusting a blood flow direction will be given. If a finger tip of the user touches this region, it is considered that the blood flow direction tool is called, and an instruction for adjusting a blood flow direction will be given. When the finger tip of the user touches pixels on a right or left end of the first line segment and regions near the pixels and rotates clockwise or counterclockwise, the first line segment also rotates clockwise or counterclockwise. A rotation angle can correspond to the movement trajectory of touch, for example, the movement trajectory of touch accounts for 500 pixels, and the end of the first line segment also moves for 500 pixels. By using the above-mentioned method, the blood flow direction tool is adjusted to be in the same direction as the blood flow direction.

(2) When a single-point touch instruction from the user in a second instruction receiving region 92 is received, a blood flow spectrum sampling line is called. During instruction input, the blood flow spectrum sampling line rotatably changes, so that an input habit of the user may also approximately rotatably changes along with a second line segment, and a movement trajectory of touch is in the third direction. The second instruction receiving region is located on the lower part of the interface. If a finger tip of the user touches the second instruction receiving region, it is considered that an instruction for adjusting a position of the blood flow spectrum sampling line will be given. When the finger tip touches the second instruction receiving region and rotates clockwise or counterclockwise, the first line segment also rotates clockwise or counterclockwise. A rotation angle can correspond to the movement trajectory of touch, for example, the movement trajectory of touch accounts for 500 pixels, and the end of the first line segment also moves for 500 pixels. By using the above-mentioned method, a sampling position on a section of a blood vessel is adjusted.

(3) When a single-point touch instruction from the user in a third instruction receiving region 93 is received, a sampling volume tool is called. Herein, a position of the sampling volume tool is changed, the sample volume tool can optionally move within a 360-degree range, and therefore, the movement direction is the fourth direction. If the finger tip of the user touches the third instruction receiving region, it is considered that an instruction for adjusting the position of the sampling volume tool will be given.

When the finger tip touches the third instruction receiving region and optionally moves, the sampling volume tool also moves synchronously, wherein the movement trajectory and position may be in one-to-one correspondence. For example, if the finger tip touches to move towards the upper right part for a movement trajectory accounting for 500 pixels, the sampling volume tool also synchronously moves towards the upper right part for 500 pixels. By using the above-mentioned method, a position of the sampling volume tool on a longitudinal section of the blood vessel is adjusted.

(4) When a multi-point touch instruction from the user in a fourth instruction receiving region 94 is received, the sampling volume tool is called to change a sampling volume or change a pulse repetition frequency value.

It should be noted that the fourth instruction receiving region 94 covers the entire interface and at least overlaps with the second instruction receiving region 92 and the third instruction receiving region 93. Whether the fourth instruction receiving region 94 overlaps with the first instruction receiving region is not important because the area of the first instruction receiving region is relatively smaller, and there are few operational conflicts. In the present example, it is set that the fourth instruction receiving region overlaps with the first instruction receiving region. Of course, the second instruction receiving region does not overlap with the third instruction receiving region. Therefore, during user input, whether to input an instruction into the fourth instruction receiving region or input an instruction into other instruction regions is distinguished depending on the number of touch points. When the multi-point touch from the user is received, the fourth instruction receiving region makes a response to the input. When single-point touch from the user is received, the first instruction receiving region and the third instruction receiving region make a response.

In one of examples, if a multi-point touch instruction from the user in the first direction on the left of the fourth instruction receiving region is received, the pulse repetition frequency value is changed. When a multi-point touch trajectory of the user is from bottom to top, the ultrasound pulse repetition frequency is increased. When the multi-point touch trajectory of the user is from top to bottom, the ultrasound pulse repetition frequency is reduced.

If a multi-point touch instruction from the user in the first direction on the right of the fourth instruction receiving region is received, the sampling volume is changed. When a multi-point touch trajectory of the user is from bottom to top, the sampling volume is increased. When the multi-point touch trajectory of the user is from top to bottom, the sampling volume is reduced.

S4: After the sampling tools are adjusted on the interface in the color Doppler ultrasound spectrum mode, the interface 2 at the sampling preparation stage is switched to an interface 3 at a blood flow spectrum display stage. The sampling instruction receiving regions are closed. That is, the first to fourth instruction receiving regions are closed. For any operation on the interface, the sampling tools will be no longer controlled, and the sampling ranges, sampling directions and pulse repetition frequencies of the sampling tools will be no longer changed.

The interface 3 at the blood flow spectrum display stage displays the blood flow ultrasound images and the blood flow spectrum images side by side to the user, and the sampling tools will be displayed as well, overlap with the blood flow ultrasound images, but are no longer controlled.

S5: A blood flow spectrum image control instruction region is generated in each of the blood flow ultrasound image display region and the blood flow spectrum image region.

S6: An instruction input by the user in the blood flow spectrum image control instruction region is received, and a position of a blood flow spectrum baseline as well as an ultrasound signal gain and a spectrum speed are changed according to the instruction, which is specifically as follows:

(1) When a single-point touch instruction from the user in an ultrasound signal gain adjustment instruction receiving region is received, an ultrasound signal gain function is called. A specific direction of the first direction is determined. When the multi-point touch trajectory of the user is from bottom to top, the gain is increased. When the multi-point touch trajectory of the user is from top to bottom, the gain is reduced. The gain is a time/distance compensation gain, and if there is ultrasound attenuation, the gain is adjusted to compensate the attenuation, so that echoes inside and on the surface of an organ are consistent.

(2) When a single-point touch instruction from the user in a spectrum speed adjustment instruction region is received, a baseline tool or a spectrum tool is called. Whether to call the baseline tool or the spectrum tool is determined by the movement trajectory of the user in the instruction region. If the touch trajectory of the user is in the first direction, it is considered that the baseline tool is called to change an up-and-down position where the baseline is located. The baseline moves up and down, and a movement distance and direction thereof correspond to the movement distance and direction of the touch trajectory of the user. For example, when the touch trajectory of the user moves downwards for 300 rows of pixels, the baseline also moves downwards for 300 rows of pixels. When the touch trajectory of the user moves upwards for 200 rows of pixels, the baseline also moves upwards for 200 rows of pixels.

If the touch trajectory of the user is in the second direction, it is considered that the spectrum speed is adjusted. Whether to increase or reduce the spectrum speed and the degree of change are determined according to a specific movement direction of the touch trajectory. For example, ten gear speeds are present for the spectrum speed. When the sliding input from the user is operated once and the touch trajectory moves leftwards, the spectrum speed is increased by one gear, and thus, it can be seen from an image that a waveform diagram of a blood flow spectrum becomes closer, and a spacing between peaks becomes smaller. When the sliding input from the user is operated once and the touch trajectory moves rightwards, the spectrum speed is reduced by one gear, and thus, it can be seen from an image that a waveform diagram of a blood flow spectrum becomes wider, and a spacing between peaks becomes larger.

The above-mentioned method is written into a readable storage medium after code programming, and this readable storage medium can be installed in any tablet computer and smartphone. Therefore, this method can be implemented in a phone.

Or, the above-mentioned method is installed in any tablet computer and smartphone by downloading an APP after code programming, and thus, this method can be implemented in a phone.

The above description is an illustrative description for the present disclosure and does not represent the protection scope of the present disclosure.

In the above-mentioned examples, each example has its own emphasis. The content not completely described in a certain example can be combined with contents shown in other examples. The above-mentioned examples are not single examples, and can form new examples under possible combinations, but the formed new examples must not depart from the core concept of the present disclosure. Furthermore, if the combination of some examples conflicts with the inventive content of this patent to form contradictions, simple combination of the examples is not allowable, and should be avoided, or the combination should be followed by conflict elimination or contradictory adjustment.

It should be noted that the examples are not limited to the only implementation method in the present disclosure, but exemplifies one or more of methods that can be implemented in the present disclosure.

Other technical solutions obtained without departing from the core concept of the present disclosure fall within the protection scope of the present disclosure.

What is claimed is:

1. An interface in a color Doppler ultrasound spectrum mode, wherein the interface is generated on a display screen coupled to a processor comprising: for the interface:
   (1) a blood flow ultrasound image display region is provided at a sampling preparation stage, and a blood flow ultrasound image display region and a blood flow spectrum image region are provided side by side at a blood flow spectrum display stage; a plurality of sampling tools configured to represent sampling ranges and sampling directions on blood flow ultrasound images are displayed at any stage, and the sampling tools overlap with the blood flow ultrasound images;
   (2) at the sampling preparation stage, a plurality of sampling instruction receiving regions are generated at a first position where a part of pixels of the sampling tools are located and other positions excluding the first position on the interface; instructions given in the sampling instruction receiving regions are configured to control the sampling tools to change sampling ranges, sampling directions and pulse repetition frequencies; and
   (3) at the blood flow spectrum display stage, the sampling instruction receiving regions are closed; a blood flow spectrum image control instruction region is generated in each of the blood flow ultrasound image display region and the blood flow spectrum image region; and instructions given in the blood flow spectrum image control instruction regions are configured to change a position of a blood flow spectrum baseline, an ultrasound signal gain and a spectrum speed.

2. The interface in the color Doppler ultrasound spectrum mode of claim 1, wherein the plurality of sampling tools comprise:
   (1) a parallelogram sampling frame, which is located in the middle of the blood flow ultrasound image display region, and configured to determine a color ultrasound image region;
   (2) a pair of horizontally-disposed parallel lines, which are located in the sampling frame, form a sampling volume tool, and are configured to mark an intravascular sampling volume;
   (3) a first line segment, which is located between the parallel lines, forms a blood flow direction tool, and is configured to mark a blood flow direction; and
   (4) a second line segment, which longitudinally passes through the sampling frame, forms a blood flow spectrum sampling line, and is configured to mark a specific sampling position on a cross section of a blood vessel.

3. The interface in the color Doppler ultrasound spectrum mode of claim 2, wherein the description that the plurality of sampling instruction receiving regions are generated on the first position where a part of pixels of the sampling tools are located and other positions excluding the first position on the interface is specifically as follows:
   (1) a first instruction receiving region for deflecting the blood flow direction tool is disposed at a position where pixels on at least one end of the first line segment and regions near the pixels are located;
   (2) a second instruction receiving region for changing a position of the blood flow spectrum sampling line on the cross section of the blood vessel is disposed on a lower part of the interface;
   (3) a third instruction receiving region for moving the sampling volume tool in any direction is disposed in the regions excluding the first instruction receiving region in the interface; and
   (4) a fourth instruction receiving region for changing a pulse repetition frequency value and a sampling volume is disposed on any one of a left part and a right part of the blood flow ultrasound image display region.

4. The interface in the color Doppler ultrasound spectrum mode of claim 1, wherein the description that the blood flow spectrum image control instruction region is generated in each of the blood flow ultrasound image display region and the blood flow spectrum image region is specifically as follows: an ultrasound signal gain adjustment instruction receiving region is generated in the blood flow ultrasound image display region, and a baseline position and spectrum speed adjustment instruction receiving region is generated in the blood flow spectrum image region; and
   the display screen is a touch screen.

5. An operation method for an interface in a color Doppler ultrasound spectrum mode, which is implemented on a display screen coupled to a processor, wherein the method comprises:
   generating a color Doppler ultrasound spectrum sampling preparation interface on the display screen, displaying blood flow ultrasound images and sampling tools to a user in the interface, and generating sampling instruction receiving regions;
   receiving instructions input into the sampling instruction receiving regions by the user, and changing one of sampling ranges, sampling directions and pulse repetition frequencies according to the instructions;
   switching from color Doppler ultrasound spectrum sampling preparation interface to a blood flow spectrum display interface, and closing the sampling instruction receiving regions;
   displaying blood flow ultrasound images and blood flow spectrum images side by side as well as sampling tools overlapping with the blood flow ultrasound images in the interface to the user;

generating a blood flow spectrum image control instruction region in each of a blood flow ultrasound image display region and a blood flow spectrum image region; and receiving an instruction input into the blood flow spectrum image control instruction region by the user, and changing a position of a blood flow spectrum baseline and one of an ultrasound signal gain and a spectrum speed according to the instruction.

6. The operation method for the interface in the color Doppler ultrasound spectrum mode of claim 5, wherein the input is a sliding input by the user on the interface, is specifically a movement input by a mouse pointer, and is a touch input by the user on a display screen with a touch function via a finger tip, wherein a slide input trajectory comprises:
  (1) a first direction of movement approximately parallel to a pixel column in the interface;
  (2) a second direction of movement approximately parallel to a pixel row in the interface;
  (3) a third direction of arc movement around the center of the interface; and
  (4) a fourth direction not belonging to the first direction, the second direction and the third direction.

7. The operation method for the interface in the color Doppler ultrasound spectrum mode of claim 6, wherein the step of receiving the instructions input into the sampling instruction receiving regions by the user, and changing one of the sampling ranges, sampling directions and pulse repetition frequencies according to the instruction specifically comprises:
  when an instruction input by the user in a first instruction receiving region is received, calling a blood flow direction tool, and rotating the blood flow direction tool;
  when an instruction input by the user in a second instruction receiving region is received, calling a blood flow spectrum sampling line, and adjusting a position on a cross section of a blood vessel;
  when an instruction input by the user in a third instruction receiving region is received, calling a sampling volume tool, and moving the sampling volume tool.

8. The operation method for the interface in the color Doppler ultrasound spectrum mode of claim 6, comprising: the touch input via the finger tip comprising single-point touch and multi-point touch; and when an multi-point touch instruction input by the user in a fourth instruction receiving region is received, calling a sampling volume tool to change a sampling volume, or change a pulse repetition frequency value.

9. The operation method for the interface in the color Doppler ultrasound spectrum mode of claim 6, wherein the step of receiving the instruction input into the blood flow spectrum image control instruction region by the user, and changing the position of the blood flow spectrum baseline and one of the ultrasound signal gain and the spectrum speed according to the instruction specifically comprises:
  when an instruction input by the user in an ultrasound signal gain adjustment instruction receiving region is received, calling an ultrasound signal gain function to adjust ultrasound signal gain intensity;
  when an instruction input by the user in a spectrum speed adjustment instruction region in a first direction is received, calling a baseline tool to change the position of the blood flow spectrum baseline; and
  when an instruction input by the user in the spectrum speed adjustment instruction region in a second direction is received, adjusting a spectrum tool to adjust the spectrum speed.

10. A color Doppler ultrasound device, comprising a display screen, a processor, a communication interface and an ultrasound transducer probe, wherein the display screen is provided with the interface in the color Doppler ultrasound spectrum mode of claim 1, and the communication interface communicates with the ultrasound transducer probe under the control of the processor.

* * * * *